US00PP34870P2

(12) United States Plant Patent
Bacon et al.

(10) Patent No.: US PP34,870 P2
(45) Date of Patent: Dec. 27, 2022

(54) GRAPEVINE PLANT NAMED 'SUGRA61'

(50) Latin Name: *Vitis vinifera*
Varietal Denomination: Sugra61

(71) Applicant: Sun World International, LLC, Bakersfield, CA (US)

(72) Inventors: Terry A. Bacon, Bakersfield, CA (US); Terrence J. Frett, Bakersfield, CA (US)

(73) Assignee: Sun World International, LLC, Bakersfield, CA (US)

( * ) Notice: Subject to any disclaimer, the term of this patent is extended or adjusted under 35 U.S.C. 154(b) by 0 days.

(21) Appl. No.: 17/581,626

(22) Filed: Jan. 21, 2022

(51) Int. Cl.
*A01H 5/08* (2018.01)
*A01H 6/88* (2018.01)

(52) U.S. Cl.
USPC ..... Plt./205
CPC ..... *A01H 6/88* (2018.05)

(58) Field of Classification Search
USPC ..... Plt./205
CPC ..... A01H 6/88
See application file for complete search history.

*Primary Examiner* — Anne Marie Grunberg
(74) *Attorney, Agent, or Firm* — Knobbe, Martens, Olson & Bear, LLP

(57) ABSTRACT

A new and distinct variety of grapevine 'Sugra61' is characterized by the production of a very large-sized, dark red and broad elliptic berry with a late season ripening date. The berries of 'Sugra61' are very firm.

1 Drawing Sheet

Latin name of the genus and species claimed: *Vitis vinifera.*

Variety denomination: 'SUGRA61'.

BACKGROUND AND SUMMARY OF THE INVENTION

This application relates to the discovery and asexual propagation of a new and distinct variety of grapevine, 'Sugra61', as herein described and illustrated. The new variety was first selected as breeder number 'GR687R' by Terry A. Bacon and Terrence J. Frett in Wasco, Kern County, Calif. in August 2016. The variety was originated by controlled hybridization.

The new variety 'Sugra61' is characterized by the production of a very large-sized, dark red and broad elliptic berry with a late season ripening date. The berries of 'Sugra61' are very firm.

The seed parent is 'Sugrathirtyeight' (U.S. Plant Pat. No. 22,431) and the pollen parent is from bulk pollen of six unpatented red grape varieties, breeder numbers 'GR331R, 'GR361R', 'GR364R', 'GR368R', 'GR369R', 'GR370R' and one patented red grape variety 'Sugrafifty' (U.S. Plant Pat. No. 29,288). The parent varieties were first crossed in April 2014. The date of first sowing was March 2015, and the date of first flowering was April 2016.

The new variety 'Sugra61' was first asexually propagated in December 2018 in Wasco, Kern County, Calif., by Terry A. Bacon and Terrence J. Frett using hardwood cuttings.

The new variety 'Sugra61' is distinguished from to its seed parent 'Sugrathirtyeight' in that while both varieties have similar shape berries, the berries of the new variety 'Sugra61' are dark red compared to the red berries of 'Sugrathirtyeight'. Further, the fruit of the new variety 'Sugra61' ripens about 29 days later, around September 1$^{st}$ compared to August 3$^{rd}$ for 'Sugrathirtyeight'. Additionally, the new variety 'Sugra61' also has a larger berry size at 11 g compared to 8 g for 'Sugrathirtyeight'.

The new variety 'Sugra61' can be distinguished from each of the seven red grape varieties of the bulk pollen parent: 'GR331R, 'GR361R', 'GR364R', 'GR368R', 'GR369R', 'GR370R' and 'Sugrafifty' (U.S. Plant Pat. No. 29,288). The fruit of the new variety 'Sugra61' ripens later than the fruit of each of 'GR331R, 'GR361R', 'GR364R', 'GR368R', 'GR369R', 'GR370R' and 'Sugrafifty.' Further, the new variety 'Sugra61' has a larger cluster size at 850 g and a larger berry weight at 11 g, compared to a cluster size of 700 g and a berry weight of 6.7 g for 'GR331R,' a cluster size of 325 g and a berry weight of 5.0 g for 'GR361R,' a cluster size of 550 g and a berry weight of 6.8 g for 'GR364R', a cluster size of 600 g and a berry weight of 7.2 g for "GR368R', a cluster size of 500 g and a berry weight of 7.0 g for "GR369R' and a cluster size of 550 g and a berry weight of 5.8 g for "GR370R'. The new variety 'Sugra61" has the same cluster size as 'Sugrafifty' but a larger berry weight of 11 g compared to 10 g for 'Sugrafifty.' Additionally, the berries of the new variety 'Sugra61' are dark red and broad elliptic compared to the red and oval berries of 'GR331R', the dark red and round berries of 'GR361R', the red and round berries of 'GR364R,' the dark purple and round berries of GR368R,' the dark purple and broad elliptic berries of 'GR369R,' the dark purple and broad elliptic berries of 'GR370R' and the red and narrow elliptic berries of 'Sugrafifty.'

The fruit of the new variety 'Sugra61' has a ripening time that is similar to that of 'Crimson Seedless' (Unpatented), but the new variety 'Sugra61' has a broad-elliptic berry shape compared to narrow-elliptic shape for the berries of 'Crimson Seedless'. Additionally, the new variety 'Sugra61' also has a larger berry size at 11 g compared to 6.2 g for 'Crimson Seedless'.

The fruit of the new variety 'Sugra61' has a similar berry shape to that of 'IFG 68-175' (U.S. Plant Pat. No. 21,664), but ripening of the berries of the new variety 'Sugra61' begins about September 1st, about 22 days later than for the berries of 'IFG 68-175'. Additionally, the new variety 'Sugra61' also has a larger berry size at 11 g compared to 7.5 g for 'IFG 68-175'.

The fruit of the new variety 'Sugra61' has a berry color like that of 'Sheegene-13' (U.S. Plant Pat. No. 20,110), but ripening of the berries of the new variety 'Sugra61' begins about September 1st, about 29 day later than for the berries of 'Sheegene-13'. The shape of the berries of the new variety 'Sugra61' is broad-elliptic compared to ovate for the berries for 'Sheegene-13'. Additionally, the new variety 'Sugra61' has a larger berry size at 11 g compared to 8 for 'Sheegene-13'.

The new 'Sugra61' variety has been shown to maintain its distinguishing characteristics through successive asexual propagations by, for example, cuttings and grafting.

Variations of the usual magnitude from the characteristics described herein may occur with changes in any of a variety of factors such as growing conditions, irrigation, fertilization, pruning, management and climatic variation.

BRIEF DESCRIPTION OF THE DRAWING

The accompanying color photographic illustration taken from a 3-year-old plant shows typical specimens of the foliage and fruit of the present new grape variety 'Sugra61'. The illustration shows the upper and lower surfaces of the leaves and exterior and sectional views of the fruit. The photographic illustration was taken shortly after the fruit was picked and the colors are as nearly true as is reasonably possible in a color representation of this type.

DETAILED DESCRIPTION OF THE PREFERRED EMBODIMENT

Throughout this specification, color names beginning with a small letter signify that the name of that color, as used in common speech, is aptly descriptive. Color names beginning with a capital letter designate values based upon The R.H.S. Colour Chart, published by The Royal Horticultural Society, London, England, 1986.

Many of the descriptive values in this specification are based on and conform to those set forth by the International Board for Plant Genetic Resources Institute Grape Descriptors (*Vitis* spp.) of 1983 and/or 1997, which was developed in collaboration with the Office International de la Vigne et du Vin (OIV) and the International Union for the Protection of New Varieties of Plants (UPOV).

The descriptive matter which follows pertains to three-year-old 'Sugra61' plants grown in the vicinity of Wasco, Kern County, Calif. during 2021, and is believed to apply to plants of the variety grown under similar conditions of soil and climate elsewhere.

VINE

General: (Measurements taken on a three-year-old plant).

*Vine size.*—Large. Height: Approximately 2.0 m. Width: Approximately 2.5 m.

*Vigor.*—Medium-high.

*Density of foliage.*—Dense.

*Productivity.*—Very productive.

*Crop load.*—Approximately 32 kg per vine after thinning.

*Own root.*—Yes.

*Training method.*—Typically cane pruned leaving 6 canes.

*Resistance.*—Neither resistance nor susceptibility to particular diseases or pests has been observed in this variety.

Trunk:

*Shape.*—Stocky.

*Diameter.*—Approximately 7.5 cm (at 30 cm above the soil line).

*Straps.*—Split-short.

*Surface texture.*—Medium shaggy.

*Inner and outer bark color.*—Inner bark about Medium Greyed-Orange 166C and weathering to about Dark Greyed-Green 197B in the outer bark.

SHOOTS

Young shoot:

*Form of tip.*—Half open.

*Intensity of anthocyanin coloration of tip.*—Medium.

*Density of prostrate hairs on tip.*—Absent or very sparse.

*Density of erect hairs on tip.*—Absent or very sparse.

*Color.*—About Medium Green 139C.

Woody shoot (observations made in the middle third of shoot):

*Attitude before tying.*—Semi-drooping.

*Growth of axillary shoots.*—Medium, about 17 to 21 cm in length.

*Internode length.*—Short, approximately 60 mm.

*Width at node.*—Approximately 13 mm.

*Cross section.*—Circular.

*Surface texture.*—Striated.

*Main color.*—About Medium Greyed-Orange 166C.

*Color of dorsal side of internode.*—About Medium Greyed-Orange 166C.

*Color of ventral side of internode.*—About Medium Greyed-Orange 166C.

*Color of dorsal side of node.*—About Medium Greyed-Orange 166C with Dark Greyed-Orange 166A around the bud.

*Color of ventral side of node.*—About Medium Greyed-Orange 166C with Dark Greyed-Orange 166A around the bud.

*Density of erect hairs on nodes.*—Absent.

*Density of erect hairs on internodes.*—Absent or Very Sparse.

*Density of prostrate hairs on internodes.*—Absent or Very Sparse.

*Density of prostrate hairs on nodes.*—Absent or Very Sparse.

Tendrils:

*Distribution on the shoot at full flowering.*—Continuous.

*Thickness.*—Approximately 3 mm.

*Color.*—About Light Yellow-Green 148D in mid-summer.

*Form.*—Bifurcated.

*Number of consecutive tendrils.*—Three or more.

*Length of tendril.*—Medium, approximately 15 cm.

LEAVES

Young leaves:

*Color of upper surface of first 4 distal unfolded leaves.*—About Medium Red 39A.

*Average intensity of anthocyanin coloration of six distal leaves prior to flowering.*—Present.

*Density of prostrate hairs between veins at lower surface of 4th distal unfolded leaf.*—Absent or very sparse.

*Density of erect hairs between veins at lower surface of 4th distal unfolded leaf.*—Absent or very sparse.

*Density of prostrate hairs on veins at lower surface of 4th distal unfolded leaf.*—Absent or very sparse.

*Density of erect hairs on veins at lower surface of 4th distal unfolded leaf.*—Absent or very sparse.

Mature leaves (observations made in the middle third of shoot):

*Average length.*—Approximately 10 cm to 12 cm.

*Average width.*—Approximately 13 cm to 15 cm.

*Shape of blade.*—Pentagonal.

*Number of lobes.*—Approximately 5.

*Mature leaf profile.*—Undulate.

*Blistering surface of blade upper surface.*—Absent or very weak.

*Leaf blade tip.*—In the plane of the leaf.

*Undulation of margin.*—Slightly undulating.

*Thickness.*—Average — typical of *Vitis vinifera* species.

*Overall shape of teeth.*—Mixture of both sides straight and both sides convex.

*Length of teeth.*—Medium, ranging from about 3 mm to 8 mm.

*Ratio length/width of teeth.*—Very small, nearly 1:1.

*General shape of petiole sinus lobes.*—Half-open.

*Tooth at petiole sinus.*—Absent.

*Petiole sinus limited by veins.*—Absent.

*Shape of upper lateral sinus lobes.*—Usually open.

*Depth of upper lateral sinuses.*—Deep, approximately 3 cm to 4 cm.

*Density of prostrate hairs between veins on lower surface of blade.*—Absent to very sparse.

*Density of erect hairs between veins on lower surface of blade.*—Absent to very sparse.

*Density of prostrate hairs on main veins on lower surface of blade.*—Absent to very sparse.

*Density of erect hairs on main veins on lower surface of blade.*—Absent to very sparse.

*Density of prostrate hairs on main veins on upper surface of blade.*—Absent to very sparse.

*Autumn coloration of leaves.*—Usually about Light Green 138B becoming about Medium Grey-Brown 199C.

Upper leaf surface:

*Color.*—About Dark Green 139A.

*Surface texture.*—Smooth, dull.

*Surface appearance.*—Dull.

*Anthocyanin coloration of main veins.*—Absent or very sparse.

Lower leaf surface:

*Color.*—About Medium Yellow-Green 146B.

*Surface texture.*—Smooth, dull.

*Surface appearance.*—Dull.

*Anthocyanin coloration of main veins.*—Absent or very sparse.

Petiole:

*Length of petiole.*—Approximately 6 cm.

*Diameter.*—Approximately 3 mm.

*Length of petiole compared to middle vein.*—Much shorter; 6 cm for the petiole compared to 11 cm for middle vein.

*Density of prostrate hairs on petiole.*—Absent.

*Density of erect hairs on petiole.*—Absent.

*Color.*—About Medium Yellow-Green 147C.

Buds:

*Shape.*—Conical.

*Size.*—Medium, approximately 3 mm wide×4 mm long.

*Position.*—Slightly held out.

*Bud fruitfulness.*—Basal, mostly fruitful.

*Time of bud burst.*—Medium, approximately March 31st for the southern San Joaquin Valley region of California.

FLOWERS

General:

*Flower type.*—Fully developed stamen and fully developed gynoecium.

*Position of first flowering node.*—Usually $4^{th}$ to $5^{th}$ node of current season growth.

*Number of inflorescences per shoot.*—Averages 1.5.

*Time of full bloom.*—Approximately May $5^{h}$ in the southern San Joaquin Valley region of California

FRUIT

General:

*Ripening period.*—Late season, beginning about September 1st in the southern San Joaquin Valley region of California.

*Use.*—Fresh market.

*Storage quality.*—Excellent.

Cluster:

*Form.*—Conical shouldered.

*Cluster size (peduncle excluded).*—Large.

*Cluster length (peduncle excluded).*—Approximately 18 cm.

*Cluster width.*—Approximately 14 cm.

*Cluster weight.*—Approximately 850 g.

*Cluster density.*—Typically dense before manipulation. Rachis not visible and berries not readily movable.

*Number of berries.*—Approximately 80-100 berries before trimming.

Peduncle:

*Length.*—Long, approximately 3 cm.

*Diameter.*—Approximately 5 mm.

*Lignification of peduncle.*—Weak.

*Color.*—About Medium Yellow-Green 146C.

Berry:

*Size.*—Very large, approximately 11 g.

*Dimensions.*—Width: Approximately 26 mm. Length: Approximately 32 mm.

*Uniformity of size.*—Uniform.

*Shape.*—Broad elliptic.

*Cross section.*—Circular.

*Skin color (without bloom).*—About Dark Red 53A when fully ripe, becoming Dark Red-Purple 59A at fully ripe.

*Flesh color.*—About Light Yellow-Green 149D as it start to ripen, becoming Light Red 38B at fully ripe.

*Anthocyanin color of flesh*.—Medium, develops darker flesh throughout as it becomes past ripe.
*Bloom* (*cuticular wax*).—Medium, typical of most commercial *Vitis vinifera*.
*Pedicel length*.—Approximately 9 mm.
*Pedicel thickness*.—Medium, approximately 1.7 mm.
*Berry separation from pedicel*.—Moderately easy.
*Seed traces*.—Berries contain 1 to 3 rudimentary soft seed traces per berry. Seed traces are about Dark Red 45B.
*Berry firmness*.—Very firm.
*Flesh juiciness*.—Very juicy.
*Flesh texture*.—Very crunchy and juicy.
*Particular flavor*.—Fruity.
*Refractometer test*.—About 18 Brix.
*Juice pH*.—About 3.56.
*Titratable acidity*.—About 0.51%.
*Brix*.—Acid Ratio: Approximately 33.

Skin:

*Skin thickness*.—Medium, about 175 μm.
*Skin texture*.—Smooth.
*Skin reticulation*.—Absent.
*Skin tenacity*.—Tenacious to flesh.
*Skin tendency to crack*.—Rare.
*Skin sensitivity to sunburn*.—None.

What is claimed is:

1. A new and distinct variety of grapevine as herein illustrated and described.

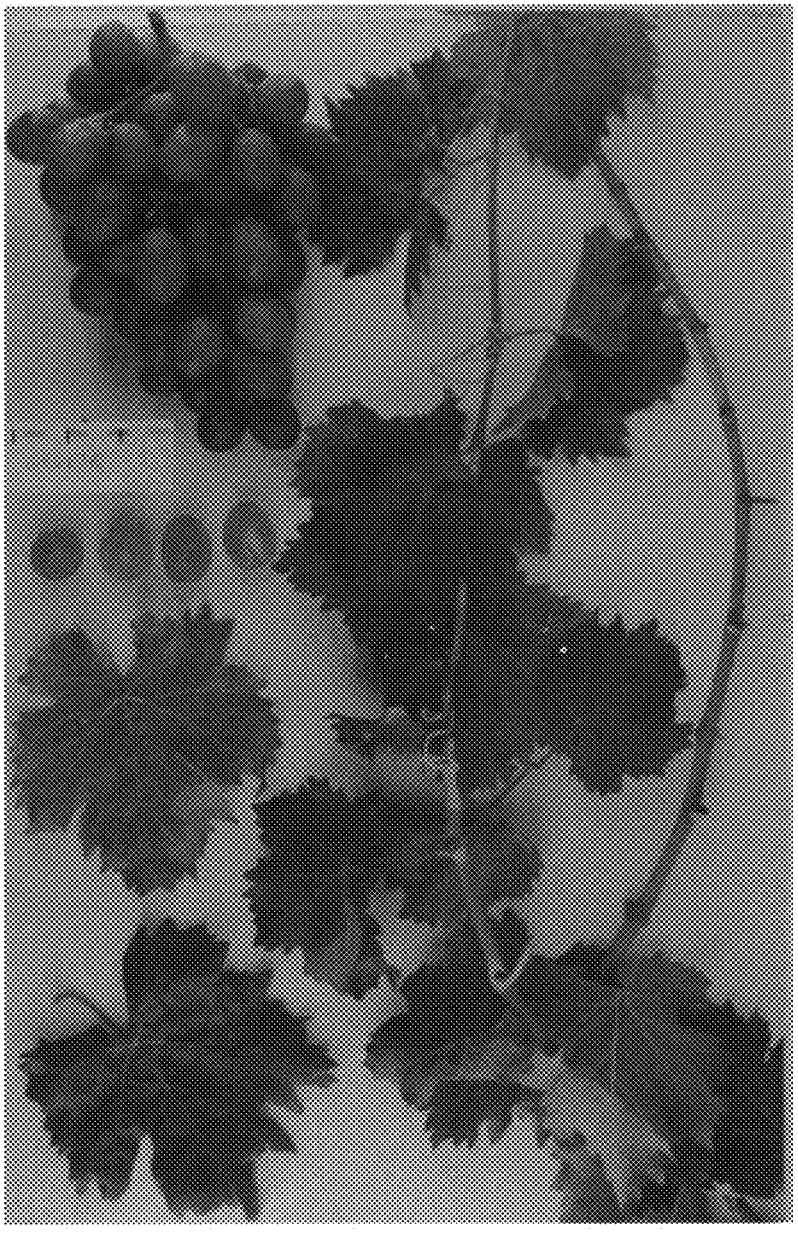

* * * * *